(12) United States Patent
Devreotes et al.

(10) Patent No.: US 10,869,908 B2
(45) Date of Patent: Dec. 22, 2020

(54) INDUCING CELL DEATH BY HYPERACTIVATION OF MOTILITY NETWORKS

(71) Applicant: The Johns Hopkins University, Baltimore, MD (US)

(72) Inventors: Peter Devreotes, Towson, MD (US); Huaqing Cai, Baltimore, MD (US); Marc Edwards, Baltimore, MD (US); Jun Liu, Clarksville, MD (US); Michele Vitolo, Baltimore, MD (US); Thomas Lampert, Baltimore, MD (US); Yu Long, Ellicott City, MD (US); Alexandra Debonnes, Meyrieu-les-Étangs (FR)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/080,975

(22) PCT Filed: Feb. 24, 2017

(86) PCT No.: PCT/US2017/019273
§ 371 (c)(1),
(2) Date: Aug. 29, 2018

(87) PCT Pub. No.: WO2017/151418
PCT Pub. Date: Sep. 8, 2017

(65) Prior Publication Data
US 2019/0060396 A1   Feb. 28, 2019

Related U.S. Application Data

(60) Provisional application No. 62/301,315, filed on Feb. 29, 2016.

(51) Int. Cl.
| | | |
|---|---|---|
| *A61K 38/12* | (2006.01) | |
| *A61K 31/47* | (2006.01) | |
| *A61K 31/5415* | (2006.01) | |
| *A61K 31/655* | (2006.01) | |
| *A61N 1/00* | (2006.01) | |
| *A61K 31/404* | (2006.01) | |
| *A61K 31/505* | (2006.01) | |
| *A61K 31/366* | (2006.01) | |
| *A61K 31/22* | (2006.01) | |
| *A61K 31/40* | (2006.01) | |
| *A61K 9/00* | (2006.01) | |
| *A61F 7/00* | (2006.01) | |
| *A61H 7/00* | (2006.01) | |
| *A61H 23/00* | (2006.01) | |

(52) U.S. Cl.
CPC .......... *A61K 38/12* (2013.01); *A61K 9/0014* (2013.01); *A61K 9/0019* (2013.01); *A61K 9/0053* (2013.01); *A61K 31/22* (2013.01); *A61K 31/366* (2013.01); *A61K 31/40* (2013.01); *A61K 31/404* (2013.01); *A61K 31/47* (2013.01); *A61K 31/505* (2013.01); *A61K 31/5415* (2013.01); *A61K 31/655* (2013.01); *A61N 1/00* (2013.01); *A61F 7/00* (2013.01); *A61H 7/00* (2013.01); *A61H 23/00* (2013.01); *C12N 2501/48* (2013.01); *C12N 2501/999* (2013.01); *C12N 2527/00* (2013.01)

(58) Field of Classification Search
CPC ...................................................... A61K 38/12
USPC ........................................................ 514/729
See application file for complete search history.

(56) References Cited

U.S. PATENT DOCUMENTS

| | | | |
|---|---|---|---|
| 8,163,691 B2 | 4/2012 | Durden | |
| 2004/0072824 A1* | 4/2004 | Telerman | A61K 31/138 514/225.8 |
| 2005/0266405 A1 | 12/2005 | Kopreski | |
| 2009/0012105 A1 | 1/2009 | Lane et al. | |
| 2010/0286241 A1 | 11/2010 | Xie et al. | |
| 2011/0081362 A1 | 4/2011 | Elledge et al. | |
| 2012/0136033 A1 | 5/2012 | Degterev et al. | |
| 2013/0131088 A1 | 5/2013 | Penn et al. | |
| 2015/0284469 A1 | 10/2015 | Simpson et al. | |
| 2016/0015709 A1 | 1/2016 | Cheresh et al. | |

OTHER PUBLICATIONS

Zhou et al., "Enhancement of CD3AK cell proliferation and killing ability by α-Thujone", International Immunopharmacology, vol. 30, pp. 57-61 (2016).*
Yasui et al., "A lipophilic statin, pitavastatin, suppresses inflammation-associated mouse colon carcinogenesis", International Journal of Cancer, vol. 121, pp. 2331-2339 (2007).*
Guijarro et al., "Lipophilic statins induce apoptosis of human vascular smooth muscle cells", Kidney International, Supplement 71, pp. S88-S91 (1999).*
Lucas et al., "Induction of programmed cell death (apoptosis) in mature lymphocytes", FEB Letters, vol. 279, No. 1, pp. 19-20 (1991).*
International Search Report dated May 19, 2017 in corresponding PCT Application No. PCT/US2017/019273.
Written Opinion of the International Searching Authority dated May 19, 2017 in corresponding PCT Application No. PC/US2017/019273.
Serrano et al. "Oncogenic ras provokes premature cell senescence associated with accumulation of p53 and p16INK4a." Cell 88(5) (1997): 593-602.

* cited by examiner

*Primary Examiner* — Kevin E Weddington
(74) *Attorney, Agent, or Firm* — Mintz Levin Cohn Ferris Glovsky and Popeo, P.C.; Peter F. Corless (57) ABSTRACT

Methods of inducing cell death by hyperactivation of motility networks are provided.

21 Claims, 9 Drawing Sheets

INDUCING CELL DEATH BY HYPERACTIVATION OF MOTILITY NETWORKS

RELATED APPLICATIONS

This application is a national stage application, filed under 35 U.S.C. § 371, of International Application No. PCT/US2017/019273 filed Feb. 24, 2017 which claims the benefit of U.S. Provisional Application 62/301,315 filed on Feb. 29, 2016. The entire contents of these applications are incorporated herein by reference in their entirety.

STATEMENT REGARDING FEDERALLY-SPONSORED RESEARCH

This invention was made with government support under GM028007 and GM034933 awarded by the National Institutes of Health. The government has certain rights in the invention.

FIELD OF THE INVENTION

This invention relates to inducing cell death in hyper-activated eukaryotic cells.

BACKGROUND OF THE INVENTION

Directed cell migration (chemotaxis) plays an important role in many physiological processes and contributes to various pathological conditions such as cancer metastasis. Migration is mediated by a network of positive and negative feedbacks among signal transduction and cytoskeletal components. Optimal migration for particular cell type requires that these networks operate within an appropriate physiological range. In diseases these networks can become hyper-activated, leading to aberrant migration and metastasis. Consequently current therapeutic strategies are aimed at restoring the normal physiological range and migration.

SUMMARY OF THE INVENTION

The invention is based, in part, upon the surprising discovery that hyper-activations of motility networks are themselves stresses or act to make cells more sensitive to external stresses which can then induce cell death. Methods of hyper-activation include, but are not limited to, combinations of activation of oncogenes and inactivation of tumor suppressor genes. External stressors include, but are not limited to, statins. Observations in such diverse cells as soil amoebae and human cells demonstrate that this discovery is a fundamental property of eukaryotic cells. This property can be exploited to selectively kill hyper-activated cells such as metastatic cancer cells and inflammatory cells.

As described in detail below, cell death by hyperactivation of a motility pathway is termed sparagmosis. Provided are methods of killing a cell with an activated motility network comprising stressing the cell or further activating or hyper-activating the cell's motility network, thereby killing the cell. For example, further activating or hyper-activating the cell induces spreading and flattening of the cell. In some cases, the method comprises administering an agent or stressor that selectively kills the cell. Preferably, the cell bears a mutated oncogene or mutated tumor suppressor gene, wherein the mutated gene comprises Ras, PI3K, PTEN, or another defined mutation that activates a cell migration pathway. For example, the stressor comprises an environmental perturbation. Exemplary environmental perturbations include a mechanical force, a temperature change, an electrical stimulus, a sound wave, osmotic shock, or other environmental change.

In some cases, the agent comprises a small molecule. A small molecule is a compound that is less than 2000 Daltons in mass. The molecular mass of the small molecule is preferably less than 1000 Daltons, more preferably less than 600 Daltons, e.g., the compound is less than 500 Daltons, less than 400 Daltons, less than 300 Daltons, less than 200 Daltons, or less than 100 Daltons. Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

Exemplary agents include a statin, a phenothiazine, an antibiotic, or an analgesic. Suitable statins include pitavastatin, fluvastatin, atorvastatin, lovastatin, pravastatin, rosuvastatin, and simvastatin. In one aspect, the statin comprises pitavastatin. In some cases, the phenothiazine comprises promazine HCl. Exemplary antibiotics include polymyxin B sulfate and chloroxine. In one aspect, the analgesic comprises phenazopyridine HCl.

The agent is administered at concentration of 0.001 mg/kg to 250 mg/kg body weight, e.g., 0.001 mg/kg, 0.05 mg/kg, 0.01 mg/kg, 0.05 mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight. In one aspect, the agent is administered at a concentration of 5 mg/kg-25 mg/kg.

In some cases, the agent is administered at least once per day, at least once per week, or at least once per month. The agent is administered for a duration of one day, one week, one month, two months, three months, six months, 9 months, or one year. In some cases, the agent is administered daily, e.g., every 24 hours. Or, the agent is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

In one aspect, the agent is administered orally, intravenously, intramuscularly, systemically, subcutaneously or by inhalation, or by other any method described herein or known to the skilled artisan. For example, the composition described herein are administered via oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

Preferably, the hyper-activation is sustained in the cell for a period of time, e.g., at least 30 minutes, at least 1 hour, at least 2 hours, at least 3 hours, at least 4 hours, at least 5 hours, at least 10 hours, at least 15 hours, at least 20 hours, at least 24 hours, or at least 2 days, at least 3 days, at least 4 days, at least 5 days, at least 6 days, or at least 7 days.

In some cases, the cell migration pathway comprises an oncogenic pathway or a tumor suppressor pathway. For example, the tumor suppressor pathway comprises PTEN. Alternatively, the oncogenic pathway comprises Ras/TorC2, Rap or PI3K.

Methods of treating a pathological condition in a subject are carried out by administering an agent or stressor that selectively kills the cell by further activating or hyper-activating the cell, thereby treating the pathological condition in the subject. Preferably, the cell bears a mutated oncogene or a mutated tumor suppressor gene. For example, the gene comprises Ras, PI3K, PTEN, or another defined mutation that activates a cell migration pathway.

In one aspect, the pathological condition comprises a neoplasia. In some cases, the subject has been diagnosed with a neoplasia or cancer. The neoplastic cell comprises a metastatic cell or a pre-metastatic cell. Exemplary cancers are selected from the group consisting of carcinoma, sarcoma, tumors, solid tumors, blood cancer, leukemia, lymphoma, skin cancer, melanoma, breast cancer, ovarian cancer, uterine cancer, prostate cancer, testicular cancer, colorectal cancer, stomach cancer, intestinal cancer, bladder cancer, lung cancer, non-small cell lung cancer, pancreatic cancer, renal cell carcinoma, kidney cancer, liver cancer, hepatocarcinoma, brain cancer, head and neck cancer, retinal cancer, glioma, lipoma, throat cancer, and esophageal cancer.

In another aspect, the pathological condition comprises an inflammatory disorder. In some cases, the subject has been diagnosed with an inflammatory disorder.

The subject is preferably a mammal in need of such treatment, e.g., a subject that has a neoplasia or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human or domesticated animal.

In one aspect, the cell undergoes fragmentation, e.g., catastrophic fragmentation.

Definitions

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

By hyper-activation is meant an activation of molecules, molecular pathways, networks of molecular pathways, cellular-processes, tissues, organs, organ systems, and organisms which is above the normal physiological level of activation.

By stressor is meant any perturbation or stimulus that causes stress to molecules, molecular pathways, networks of molecular pathways, cellular-processes, tissues, organs, organ systems, and organisms.

By motility networks is meant the molecular events and interconnections which are involved in bringing about cellular motility.

By signal transduction is meant all of the events and interactions between molecules, molecular pathways, networks of molecular pathways, which bring about changes in cellular-processes.

By cytoskeletal is meant the molecules that bring about motility and structure of the cell which include, but are not limited to actin, microtubules, and intermediate filaments.

By positive feedback is meant by a process in which change is amplified into a larger response.

By negative feedback is meant by a process in which one change leads to another change that attenuates the initial change.

By physiological is meant by a normal process that occurs in cells, tissues, organs, organ systems, and organisms. This is in opposition to pathological which is an abnormal condition in cells, tissues, organs, organ systems, and organisms.

By "agent" is meant any small compound, antibody, nucleic acid molecule, polypeptide, or fragments thereof.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term, "metastasis" or "metastatic" refers the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. After the tumor cells come another site, they continue to multiply, and eventually another tumor is formed. At the new site, the cells establish a blood supply and can grow to form a life-threatening mass. In some aspects, this new tumor is referred to as a metastatic (or secondary) tumor. The term metastatic tumor refers to a tumor that is capable of metastasizing, but has not yet metastasized to tissues or organs elsewhere in the body. In some aspects, the term metastatic tumor refers to a tumor that has metastasized to tissues or organs elsewhere in the body. In certain embodiments, metastatic tumors are comprised of metastatic tumor cells. The "metastatic sample" is used in the broadest sense, refers to a sample in which the cancer cells from a primary tumor or the cancer cells from another part of the body have spread.

By "neoplasia" is meant a disease or disorder characterized by excess proliferation or reduced apoptosis. Alternatively, the terms "tumor," "solid tumor," "primary tumor," and "secondary tumor" can also be used to refer to carcinomas, sarcomas, adenomas, and cancers of neuronal origin and, in fact, to any type of cancer which does not originate from the hematopoietic cells. Illustrative neoplasms for which the invention may be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

The term "pre-metastatic" refers to a sample in which no cancer cells from a primary tumor or from another part of the body have been detected. In some aspects, the pre-metastatic sample refers to an organ or tissue that is in the phase before the spread of cancer cells from a primary tumor or from another part of the body to this organ or tissue. Examples of pre-metastatic samples include, but are not limited to, lung, liver, brain, ovary, bone, bone marrow and lymph node.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

By "reduces" is meant a negative alteration of at least 5%, 10%, 25%, 50%, 75%, or 100%.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The term "sample," as used herein, refers to a biological sample obtained for the purpose of evaluation in vitro. In the methods of the present invention, the sample or patient sample may comprise any body fluid including, but not limited to, blood, serum, plasma, urine, saliva, and synovial fluid. A sample may also comprise any cells, tissue samples or cell components (such as cellular membranes or cellular components) obtained from a patient including a tissue biopsy.

The term "selective" is used to describe agents having greater than 10-fold, preferably greater than 100-fold, and most preferably greater than 1,000-fold activity for one target of interest over another target.

The term, "statin" as described herein, refers to a class of cholesterol lowering drugs that inhibit the enzyme HMG-CoA reductase. Statins act by competitively inhibiting HMG-CoA reductase, the first committed enzyme of the mevalonate pathway. A variety of natural statins are produced by *Penicillium* and *Aspergillus* fungi as secondary metabolites. These natural statins probably function to inhibit HMG-CoA reductase enzymes in bacteria and fungi that compete with the producer. Exemplary statins approved for use in the U.S. include atorvastatin (Lipitor), fluvastatin (Lescol), lovastatin (Mevacor), pravastatin (Pravachol), rosuvastatin (Crestor), and pitavastatin (Livalo).

By "subject" is meant a mammal, including, but not limited to, a human or non-human mammal, such as a bovine, equine, canine, ovine, or feline.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Any compositions or methods provided herein can be combined with one or more of any of the other compositions and methods provided herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. GenBank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A and FIG. 1B show photomicrographs illustrating the chemotactic responses of Dictyostelium and human neutrophils.

FIG. 2 is a cartoon showing the integration of motility, polarity and directional sensing in directed migration. Motility was achieved by spontaneous extension and retraction of pseudopods every few minutes. Polarity refers to an asymmetric distribution of cytoskeletal and signaling molecules and increased sensitivity to chemoattractant at the "front". Directional sensing can occur even in immobilized cells as evidenced by the rapid rearrangement of internal proteins in response to changes in external gradients.

FIG. 4A-FIG. 4C shows the phenotype caused by a combination of perturbations.

FIG. 6 is a series of images showing an example of a cell undergoing sparagmosis. Left, at t=0 a pten– cell expressing tet-inducible $RasC^{Q62L}$ displayed the typical multiple projection phenotype of a pten– cell. Middle, doxycycline was added to induce the expression of $RasC^{Q62L}$ and the cell adopted a spread phenotype within 8 hours. Right, after a series of ingressions, the fragmentation occurred at 27 hours. Cartoon at the bottom depicts the morphological transitions a pten– cell underwent after induction of $RasC^{Q62L}$, leading to cell death. There were several cycles of cortical ingression and recovery before cell death occurred (as indicated by the recycle arrow).

FIG. 7 is a diagram showing the process of drug library screen. The initial screen included 2560 compounds from the Johns Hopkins drug library, among which 63 were found to affect the growth of Dictyostelium pten– cells. Secondary screen confirmed nine compounds with effects selective for pten– but not wild-type cells.

DETAILED DESCRIPTION OF THE INVENTION

Directed cell migration (chemotaxis) plays an important role in many physiological processes and contributes to various pathological conditions such as cancer metastasis. Migration is mediated by a network of positive and negative feedbacks among signal transduction and cytoskeletal components. Optimal migration for a particular cell type requires that these networks operate within an appropriate physiological range. In diseases these networks can become hyper-activated, leading to aberrant migration and metastasis. Consequently current therapeutic strategies are aimed at restoring the normal physiological range and migration.

In contrast, this invention is based, in part, upon the surprising discovery that hyper-activations of motility networks are themselves stresses or act to make cells more sensitive to external stresses which can then induce cell death. Methods of hyper-activation include, but are not limited to, combinations of activations of oncogenes and inactivation of tumor suppressor genes. External stressors include, but are not limited to, statins. Observations in such diverse cells as soil amoebae and pre-metastatic cells demonstrate that this sensitivity is a fundamental property of eukaryotic cells. This property can be exploited to selectively kill hyper-activated cells such as certain metastatic cancer cells and certain inflammatory cells.

BACKGROUND

Directed cell migration (chemotaxis) plays a fundamental role in many physiological processes and contributes to various pathological conditions such as cancer metastasis (Theveneau E, Mayor R. 2012. *Developmental Biology* 366 (1):34-54, Richardson B E, Lehmann R. 2010. *Nat Rev Mol Cell Biol* 11 (1):37-49, and Sixt M. 2011. *Immunol Lett* 138 (1):32-34). During embryogenesis chemoattractants and mechanical forces guide primordial germ cells to proper locations, mediate the formation of organs, and control the wiring of the nervous system. In the adult, directed migration is critical for immune cell trafficking, wound healing, and stem cell homing to niches. It is also involved in the pathology of numerous diseases (Kolaczkowska E, Kubes P. 2013. *Nat Rev Immunol* 13(3):159-175, Zernecke A, Weber C. 2010. *Cardiovasc Res* 86(2):192-201, Bravo-Cordero J J, et al., 2012. *Curr Opin Cell Biol* 24 (2):277-283 and Roussos E T, et al., 2011. *Nat Rev Cancer* 11 (8):573-587). The migration of immune cells contributes to inflammatory disorders such as asthma, arthritis, and vascular disease. In cancer metastasis, cells escape the primary tumor, circumventing surgical intervention. These cells can enter the circulation and then migrate out to new sites in target organs. Like other fundamental cell biological processes, networks of signal transduction and cytoskeletal pathways are involved and therapeutic approaches directed at multiple targets are likely to be more effective. A systems approach to understanding and controlling directed migration is the most effective for ultimately designing unique, combined therapeutic strategies.

*Dictyostelium* as a Discovery Vehicle

*Dictyostelium* is a soil-dwelling amoeba, known for its remarkable life cycle consisting of a unicellular and multicellular phase. It is present in most terrestrial ecosystems as a normal and often abundant component of the soil microflora, and plays an important role in the maintenance of balanced bacterial populations in soils. The unicellular phase consists of solitary amoebae feeding on bacteria and reproducing by binary fission. When challenged by starvation, the amoebae collect into aggregates and develop into multicellular fruiting bodies. Its complex life cycle, ease of maintenance, and genetic and cell biological accessibility makes *Dictyostelium* an idea model organism for laboratory studies of a wide range of biological problems including signal transduction, chemotaxis, and cellular differentiation.

Chemotaxis is a Fundamental Cellular Process

Chemotaxis is a vital process in which organisms efficiently respond to the changes in the chemical composition of their environment, moving toward chemically favorable environments while avoiding unfavorable environments. It is a major process in normal physiology and in the pathogenesis of many diseases. The classic view of chemotaxis implies that motility arises from the activity of the actin/myosin cytoskeletal network and that a short, linear signal transduction pathway proceeding from chemoattractant receptors to Rac family GTPases to actin polymerization guides the process. However, it is now recognized that Ras proteins, phosphatidylinositol 3,4,5 phosphate (PIP3), TORC2, and components of other signal transduction pathways are important, conserved intermediates (Cai, H., et al., 2010. *J. Cell Biol.* 190:233-245, Lee S, et al., 1999. *Mol Biol Cell* 10(9):2829-2845, Kamimura Y, et al., 2008. *Current Biology* 18 (14):1034-1043, Bosgraaf L, et al., 2008. *J Cell Sci* 121(21):3589-3597, Liu L, et al., 2010. *Developmental Cell* 19 (6):845-857, Chen L, et al., 2003. *Mol Biol Cell.* 14(12), 5028-5037 and Iijima, M and Devreotes, P N. 2002. *Cell.* 109, 599-610). Furthermore, the prevailing view of chemotaxis implies that the role of signal transduction is merely to guide an autonomously active motile machinery. However, a new paradigm for motility and chemotaxis is emerging that signal transduction pathways control cell morphology and random motility not just guidance (Iijima, M and Devreotes, P N. 2002. *Cell.* 109, 599-610, Sasaki A T, et al., 2007. *J Cell Bio.* 178(2):185-191, and Postma M, et al., 2004. *J Cell Sci.* Jun. 15; 117(Pt 14):2925-35).

Knowledge of the signal transduction networks that regulate cell migration is still evolving, but it already has significant implications. Many important oncogenes and tumor suppressors, such as Ras, PI3K, and PTEN, are involved. Ras is a superfamily of small G proteins (guanosine-nucleotide-binding proteins) which are ubiquitously expressed in all cell lineages and organs and functions as a binary signaling switch with select on and off states. The human oncogenic members of the Ras family have been reviewed (Rojas, et al., *J Cell Biol* 196, no. 2 189-201, and Karnoub, et al., *Nat Rev Mol Cell Biol.* 2008, Jul. 9(7): 517-531, both of which are incorporated herein by reference), and in general they regulate cell proliferation, differentiation, morphology, and apoptosis. PI3K are a family of enzymes also involved in cell growth and survival as well as motility. PI3Ks phosphorylate the 3-position hydroxyl group of the inositol ring of phosphatidylinositol-4,5-trisphosphate ($PIP_2$) to form phosphatidylinositol-3,4,5-trisphosphate ($PIP_3$). PTEN is a phosphatidylinositol-3,4,5-trisphosphate 3-phosphatase that negatively regulates PI3K signaling by dephosphorylating the PIP3. In many cancers, oncogenic PIK3CA is activated or tumor suppressor PTEN is inactivated and this pathway is overactive, thus reducing apoptosis and allowing proliferation. Orthologs of Ras, PI3K, PTEN and many other components involved in chemotaxis have been identified in many metazoans and strong orthologs are present in *Dictyostelium*.

Statins are Well Established Drugs

Statins are a class of cholesterol lowering drugs that inhibit the enzyme HMG-CoA reductase which plays a central role in the production of cholesterol. High cholesterol levels have been associated with cardiovascular disease (CVD), and statins have been found to prevent cardiovascular disease and mortality in those who are at high risk. Statins act by competitively inhibiting HMG-CoA reductase, the first committed enzyme of the mevalonate pathway. Because statins are similar in structure to HMG-CoA on a molecular level, they fit into the enzyme's active site and compete with the native substrate (HMG-CoA). This competition reduces the rate by which HMG-CoA reductase is able to produce mevalonate, the next molecule in the cascade that eventually produces cholesterol. A variety of natural statins are produced by *Penicillium* and *Aspergillus* fungi as secondary metabolites. These natural statins probably function to inhibit HMG-CoA reductase enzymes in bacteria and fungi that compete with the producer.

Figure 1A:
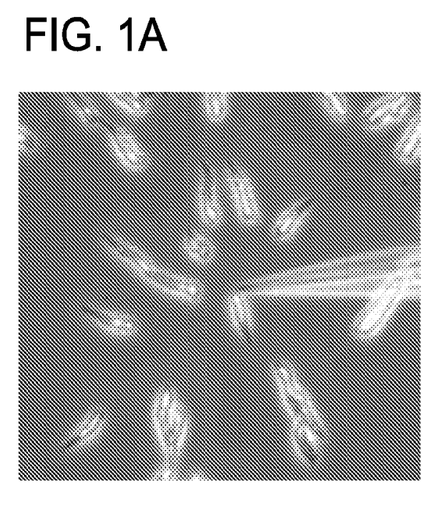
FIG. 1A shows Dictyostelium moving towards the cyclic adenosine monophosphate (cAMP)-filled micropipette.
Figure 1B:
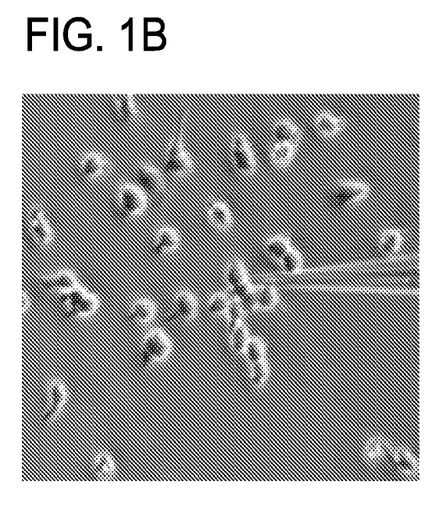
FIG. 1B shows HL-60 human neutrophils moving towards the peptide, fMLP (N-Formylmethionyl-leucyl-phenylalanine). Images were taken 20 minutes after pipettes were placed in fields of distributed cells. Gradients were about 20% across the lengths of the 15 µm cells.

Example 1: Mechanisms of Migration and Chemotaxis Discovered in *Dictyostelium* are Operative in Human Leukocytes Many of the mechanisms of cell migration and chemotaxis were initially discovered in one of the most extensively studied model systems, *Dictyostelium*, and later found to be operative in higher eukaryotic cells (FIG. 1A and FIG. 1B).

Figure 2:
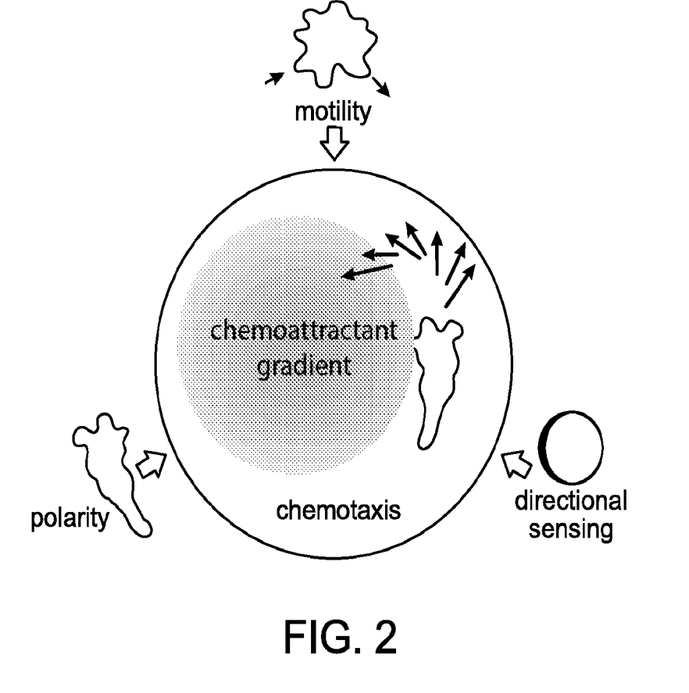

*Dictyostelium* cells, human leukocytes, and metastasizing cancer cells displayed "amoeboid" movement, rhythmically extending pseudopods which intermittently pulled the cells forward whereas the "mesenchymal" motility of fibroblasts was characterized by the gliding lamellipodia (Friedl P, et al., 1998. Microsc Res Tech 43(5):369-378). Guidance signals for migrating cells acted through GPCRs, RTKs, and other receptor classes or were derived from substrate stiffness, electric fields, or light or temperature gradients. Nevertheless, many of the signal transduction and cytoskeletal events that occurred selectively on the leading and trailing edges of migrating cells were the same. During directed migration, integration of motility, polarity and directional sensing was observed, although each of these processes was also observed separately (FIG. 2). For example, cells moved randomly by spontaneously extending pseudopodia in the absence of a chemoattractant gradient. Cells had a stable axis of polarity and were more sensitive to the chemoattractant at the front which allowed them to migrate efficiently. However, less polarized cells still migrated directionally and reacted more quickly to shifting cues Immobilized cells maintained their ability to sense directional cues by localizing proteins toward or away from the gradient. The polarity of static cytoskeleton in the immotile cells also retained polarized sensitivity. These and other similarities indicated that common mechanisms evolved in the earliest eukaryotic cells and have been remarkably conserved (Artemenko, Y., et al., P. N. 2014. Cell Mol Life Sci. October; 71(19):3711-47). Research in *Dictyostelium* and other model organisms continues to contribute to the understanding of migration and chemotaxis.

Figure 3:
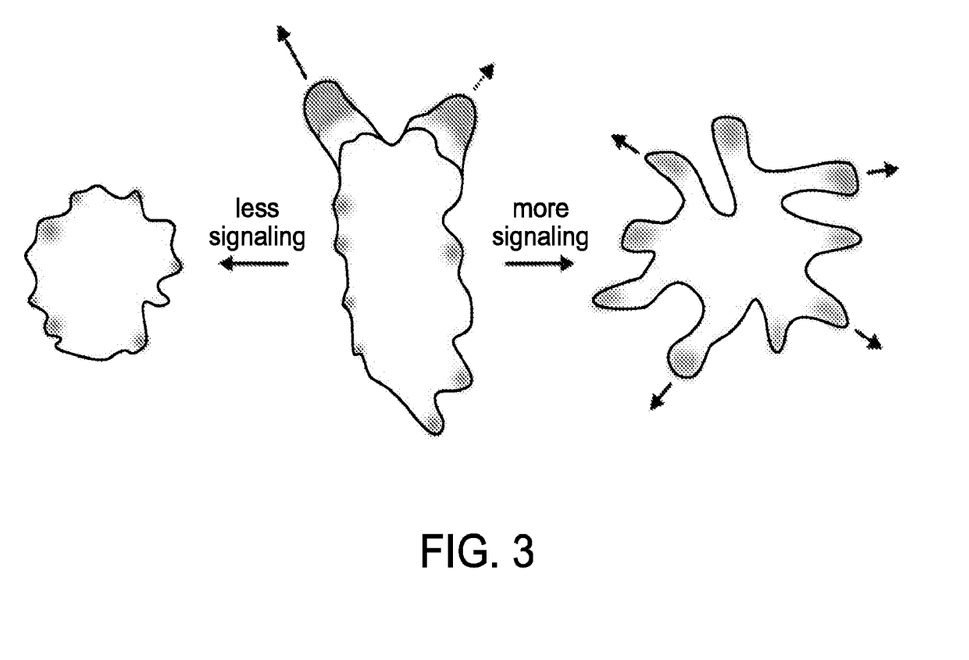
FIG. 3 is a cartoon showing the optimal activation of the signal transduction network that drives cell migration. The cartoon shows cell morphology and fluorescent reporters of signal transduction (green) or cytoskeletal (orange) activity on the basal surface of cells. Decreasing signal transduction by deleting TORC2 subunits and inhibiting PI3K blocks migration. Increasing signal transduction activity by deleting PTEN (phosphatase and tensin homolog) or by expressing a constitutively active version of Ras also impairs cell migration by promoting too many projections.

Example 2: An Optimal Amount of Spontaneous Activation of the Signal Transduction Network Acts as the "Pacemaker" for Cell Migration and Defects that Cause Excessive Cell Spreading are Additive The essential roles of signal transduction events in motility and the optimal activation of the signal transduction network to drive cell migration were evaluated (FIG. 3). In amoeboid cells, such as *Dictyostelium* and human neutrophils, the signal transduction network was excitable and "fired" stochastically every few minutes, initiating waves of activity that propagate along the cell surface even in the absence of the cytoskeleton (Xiong Y et al., 2010 Proc Natl Acad Sci 107(40), 17079; Huang et al., 2013 Nat Cell Biol 15(11), 1307; Asano Y et al., 2008, 65(12) 923; Gerisch G. et al. 2012, Biophys J. 103(6), 1170; Weiner, O D et al., 2007 PLoS Biol., 5(9); Arai Y et al., 2010 Proc Natl Acad Sci 107(27), 12399; Taniguchi D et al., 2013 Proc Natl Acad Sci, 110(13), 5016). Without input from the signal transduction network, the cytoskeletal network displayed oscillations at local regions which caused only weak undulations on the cell perimeter (Huang et al., 2013 Nat Cell Biol 15(11), 1307).

The coupling of the signal transduction and cytoskeletal networks leads to pseudopod extension. Thus, an optimal amount of spontaneous activation of the signal transduction network acted as the "pacemaker" for cell migration (FIG. 3). If several signal transduction pathways were blocked simultaneously, e.g. deleting TORC2 subunits and inhibiting PI3K, cytoskeletal oscillations still occurred, but cells did not extend pseudopods or migrate (Huang et al., 2013 Nat Cell Biol 15(11), 1307). However, if signal transduction events were so elevated that they overrode polarity, pseudopods were extended simultaneously along the perimeter and the cell also did not move (Cai H et al., 2010 J. Cell Biol. 190, 233; Iijima M et al., 2002 *Cell* 109, 599). For example, deleting PTEN or expressing a constitutively active version of Ras impaired cell migration by promoting too many projections.

Figure 4A:
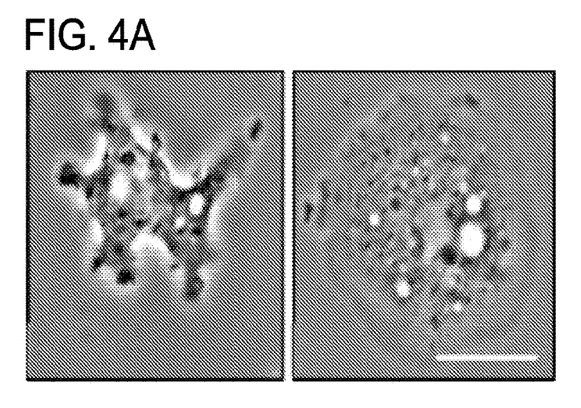
FIG. 4A is a photomicrograph showing the expression of constitutively active $RasC^{Q62L}$ induced with a "tet-on" promoter in pten– cells. Cell is shown before (left) and 8 hours after (right) addition of doxycycline. Scale bar is 18 µm.
Figure 4B:
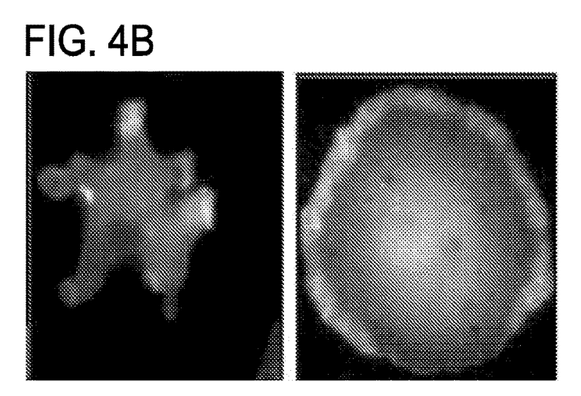
FIG. 4B is a photomicrograph showing cells expressing fluorescent F-actin biosensor, GFP-LimE. Actin is recruited to the pseudopods in pten– cells whereas it is elevated globally around the perimeter in $RasC^{Q62L}$/pten– cells.
Figure 4C:
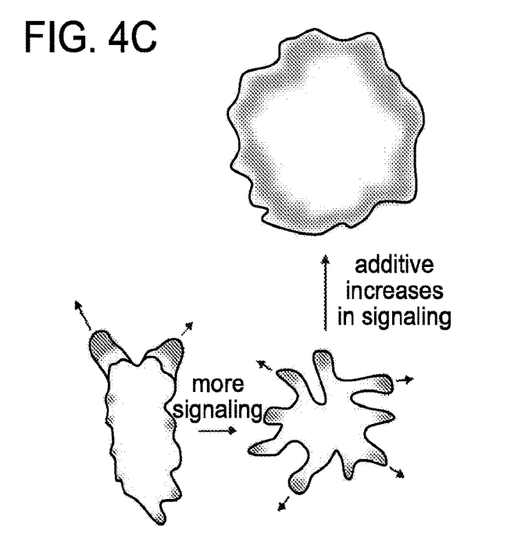
FIG. 4C is a cartoon showing that synergistic over activation of signal transduction and/or cytoskeletal networks lead to formation of spread cells (as compared to FIG. 3).

Research into the parallel pathways of the signal transduction network led to the discovery that defects that cause excessive cell spreading were additive. Ras/TORC2 and PI3K pathways were constitutively activated by expressing RasC$^{Q62L}$ in cells lacking PTEN. As noted earlier, RasC$^{Q62L}$ expression or PTEN depletion each caused an increase in lateral pseudopod formation (FIG. 3); however, the combination yielded a phenotype much stronger than that caused by either individual perturbation. The combination of the two perturbations produced extremely spread and flattened cells, with the entire perimeter consisting of a continuous "pseudopod" (FIG. 4).

Figure 5:
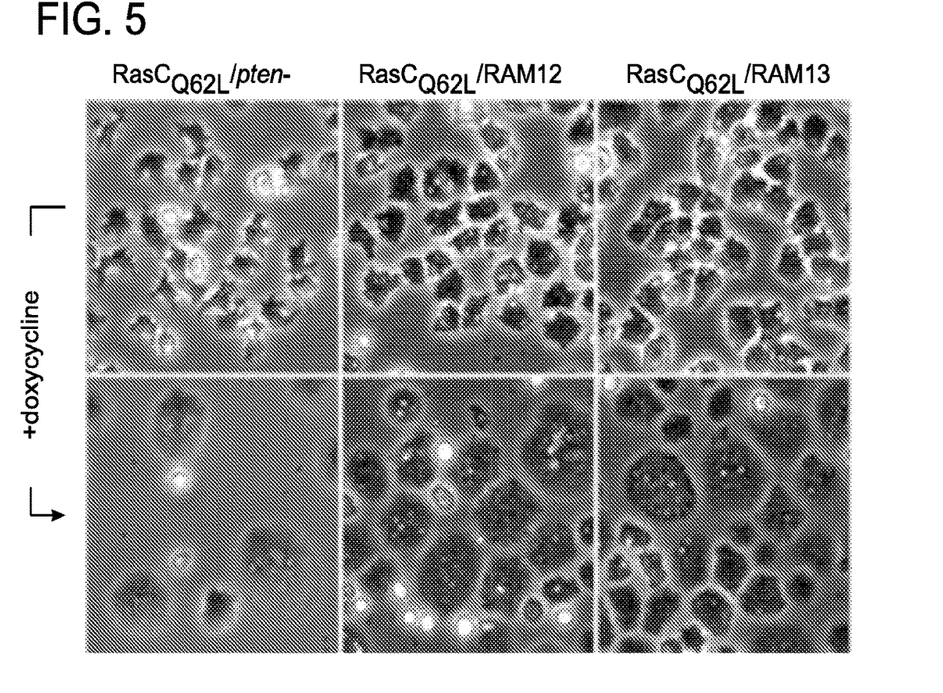
FIG. 5 is a series of photomicrographs showing examples of the conversion of RAM (Regulators of Adhesion and Motility) mutant to the spread cell phenotype. Tet-inducible $RasC^{Q62L}$ was expressed in pten–, RAM12, or RAM13 cells. Fields of cells are shown before and 20 hours after induction of $RasC^{Q62L}$. More than 80% of the cells displayed a flattened phenotype after induction. Average diameters of pten–, RAM12, and RAM13 cells increased from 28.7±4.1, 27.8±5.1 and 27.8±5.0 µm before induction to 49.0±7.3, 45.5±8.6, and 46.8±7.9 µm following induction, respectively.

Example 3: Signals from Multiple Pathways Impinging on the Cytoskeleton are Integrated to Generate the Flattened Phenotype The phenotype did not depend specifically on the RasC/TORC2 or PI3K pathways. Rather, signals from multiple pathways impinging on the cytoskeleton can be integrated to generate the phenotype. RAM (Regulator of Adhesion and Motility) mutants were isolated in a screen for regulators of cell morphology and migration. Mutant cells were more spread and adhered more strongly than wild-type cells. Most of the mutants also displayed strong defects in cell motility and chemotaxis. When constitutively active RasC$^{Q62L}$ was expressed in the RAM mutants, these cells also formed extremely spread cells like those seen in the pten− cell background (FIG. 5). In another example, Rap1 is a small GTPase that controls cell adhesion in a variety of cell types. When constitutively active Rap1A$^{G12V}$ was expressed in pten− or RAM cells, a similar phenotype was observed.

Figure 6:
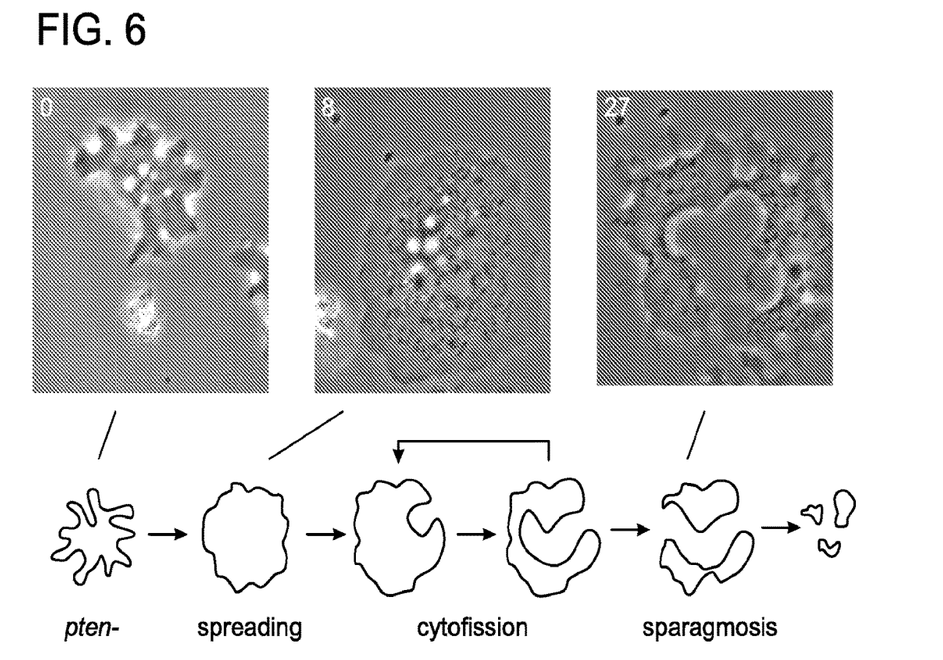

Example 4: Hyper-Activation of the Signal Transduction Network Results in Cell Fragmentation and Death The expression of RasC$^{Q62L}$ in pten− cells maintained for an additional 16-28 hours resulted in cells that underwent a catastrophic fragmentation and death (FIG. 6). It was verified that 98% of the induced cells were dead by Trypan Blue staining and their failure to form foci on re-plating. The surviving 2% of cells were not flattened, indicating that they lost expression of RasC$^{Q62L}$. This observed mode of cell death has not been elucidated before in either *Dictyostelium* or in mammalian cells. This mechanism was named "sparagmosis" from the Greek sparasso, meaning "tear, rend, or pull to pieces." Other pairwise combinations of perturbations that generated flattened cells such as expression of RasC$^{Q62L}$ in RAM mutants or expression of Rap1A$^{G12V}$ in pten− also led to similar cell death by fragmentation.

Example 5: Screen to Identify Compounds that Selectively Kill Pten− Cells

The observation that further activation of the signal transduction network in pten-cells resulted in cell death prompted screening for small molecules that specifically targeted cells with PTEN mutation. Since PTEN is one of the most commonly mutated tumor suppressors in human cancer, the molecules identified in the screen will provide a new way of confronting metastatic and pre-metastatic cancer cells.

Figure 7:
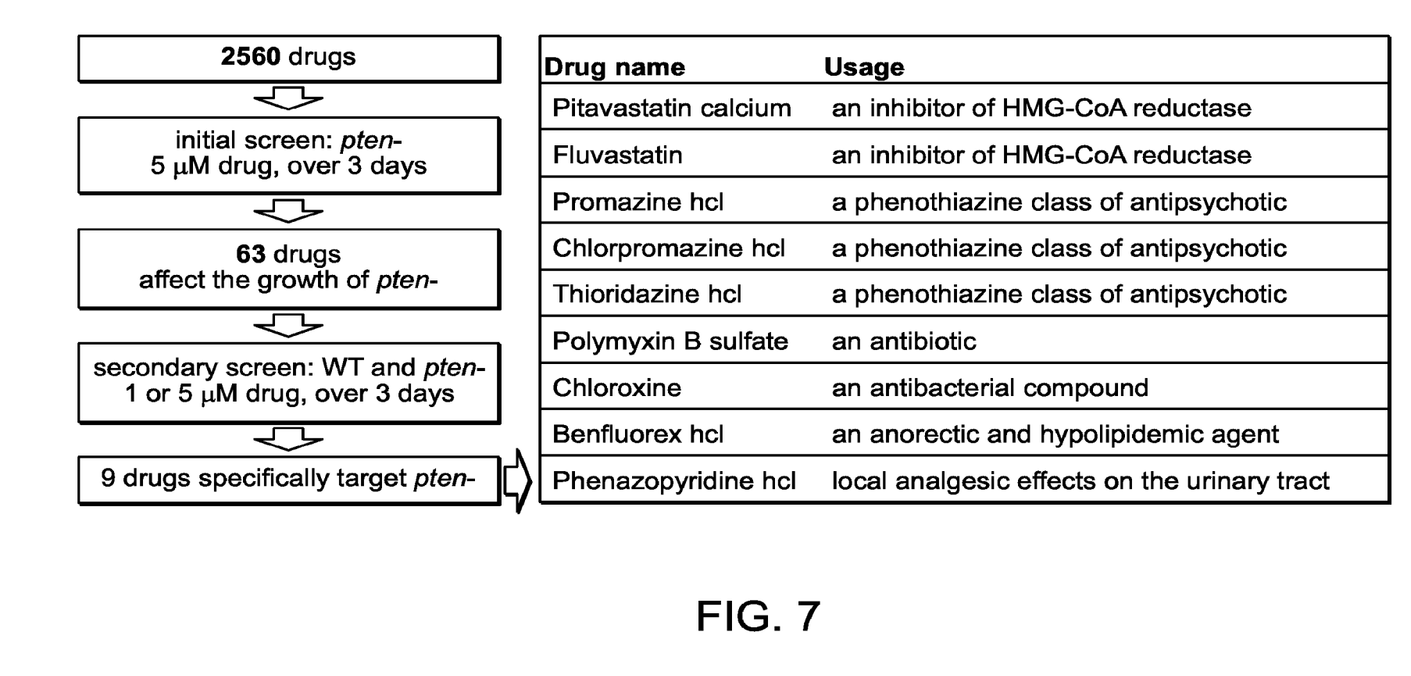

The John Hopkins Drug Library contains 2560 drugs that are either FDA approved, have been proven in other countries for treating human diseases, or have entered phase II clinical trials. In a phenotypic screen using the library, nine compounds were found to selectively slow down the growth of or kill pten− cells (FIG. 7). These compounds fell into several classes: certain phenothiazines (promazine, chlorpromazine, and thioridazine), certain antibiotics (polymyxin and chloroxine), certain statins (fluvastatin and pitavastatin), and others (benfluorex and phenazopyridine). All of the hits were validated independently with purchased compounds and repeating the experiments. Importantly, these drugs had little or no effect on the morphology and growth of wild type cells.

Figure 8:
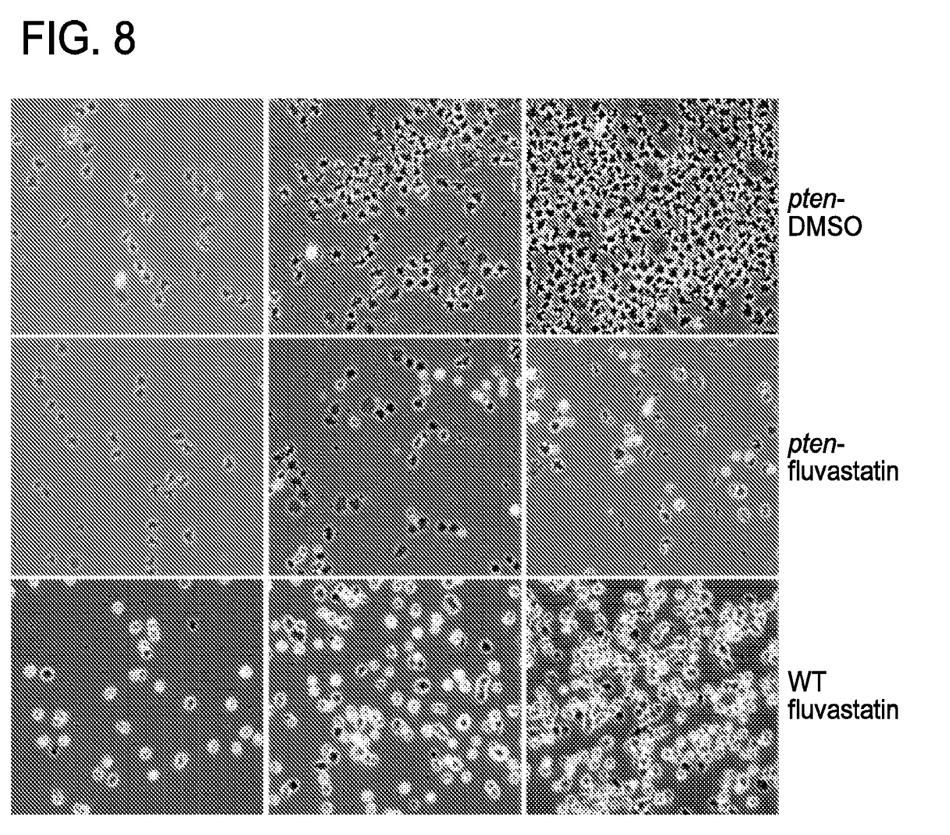
FIG. 8 is a series of photomicrographs showing that fluvastatin selectively affected the growth and survival of Dictyostelium pten– cells. Cells were treated with 5 µM fluvastatin or DMSO. Images were taken 17 hours (left), 41 hours (middle), and 65 hours (right) after drug treatment.

In particular, the two statins, fluvastatin (trade name Lescol) and pitavastatin (Livalo) displayed high cytotoxicity for *Dictyostelium* pten− cells (FIG. 8, fluvastatin shown as an example). Compared to cells treated with DMSO control, which continued to grow over a three day period, pten− cells treated with fluvastatin and pitavastatin grew much slower. Cell death started to occur around 40 hours after drug treatment and a marked increase was observed in the following 24 hours. In contrast, wild type cells treated with the statins showed no significant growth defect.

Figure 9:
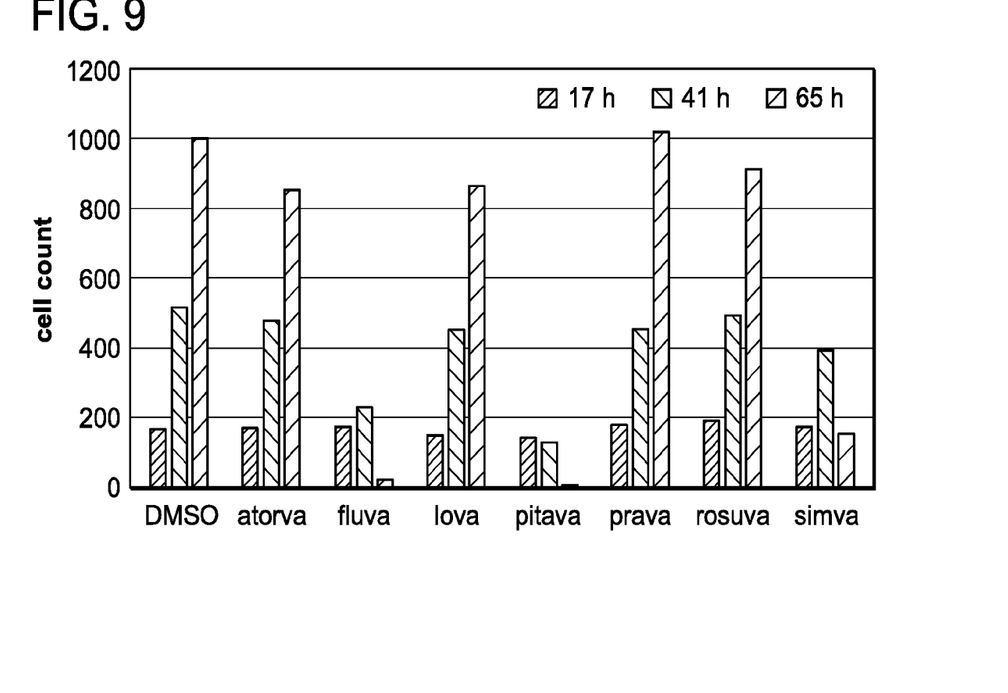
FIG. 9 is a bar graph showing statins that specifically target Dictyostelium pten– cells. Seven statins currently available on the market were tested for cytotoxicity on pten– cells. The graph quantifies growth of cells treated with 5 µM of statins or DMSO control over a three day period. Blue, orange, and yellow bars represent relative cell counts 17 hours, 41 hours, and 65 hours after drug treatment.

Statins are inhibitors of HMG-CoA reductase, the rate-controlling enzyme of the mevalonate pathway. In addition to fluvastatin and pitavastatin, the other statins currently available on the market include atorvastatin (Lipitor), lovastatin (Mevacor, Altocor), pravastatin (Pravachol), rosuvastatin (Crestor), and simvastatin (Zocor). All the other five statins were tested for their cytotoxicity on pten− cells (FIG. 9). Fluvastatin and pitavastatin displayed higher efficacy compared to all other statins. Cell death was also observed with simvastatin treatment, whereas the other four statins were well tolerated.

Figure 10:
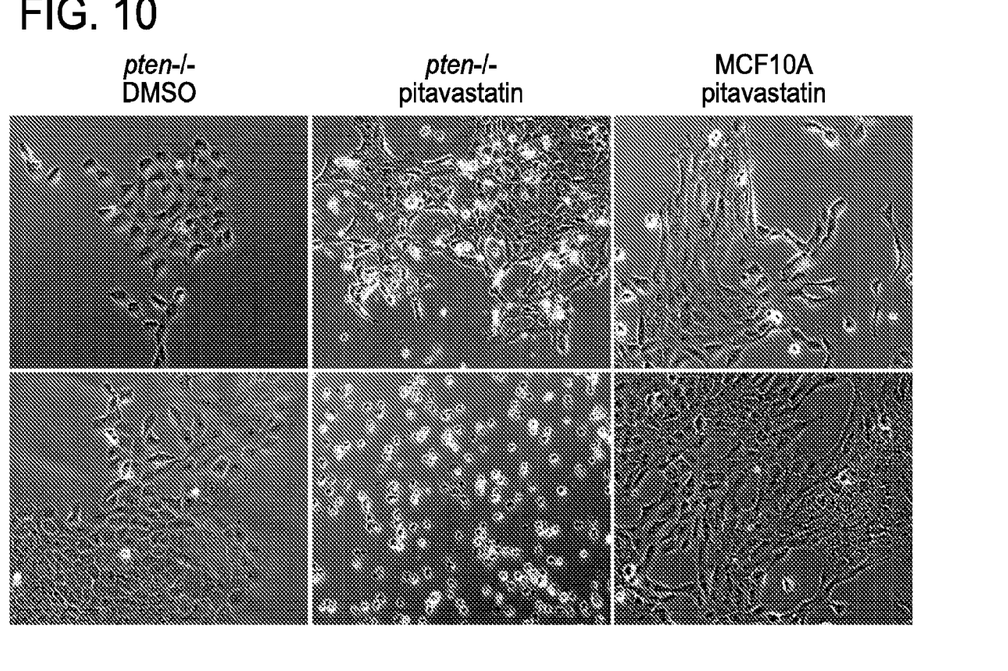
FIG. 10 is a series of photomicrophotographs showing cell death induced by pitavastatin in MCF-10A cells bearing a homozygous PTEN deletion. MCF-10A or pten–/– cells were treated with DMSO control or 5 µM pitavastatin. Upper and lower panels show 44 hours and 68 hours after drug treatment.
Figure 11:
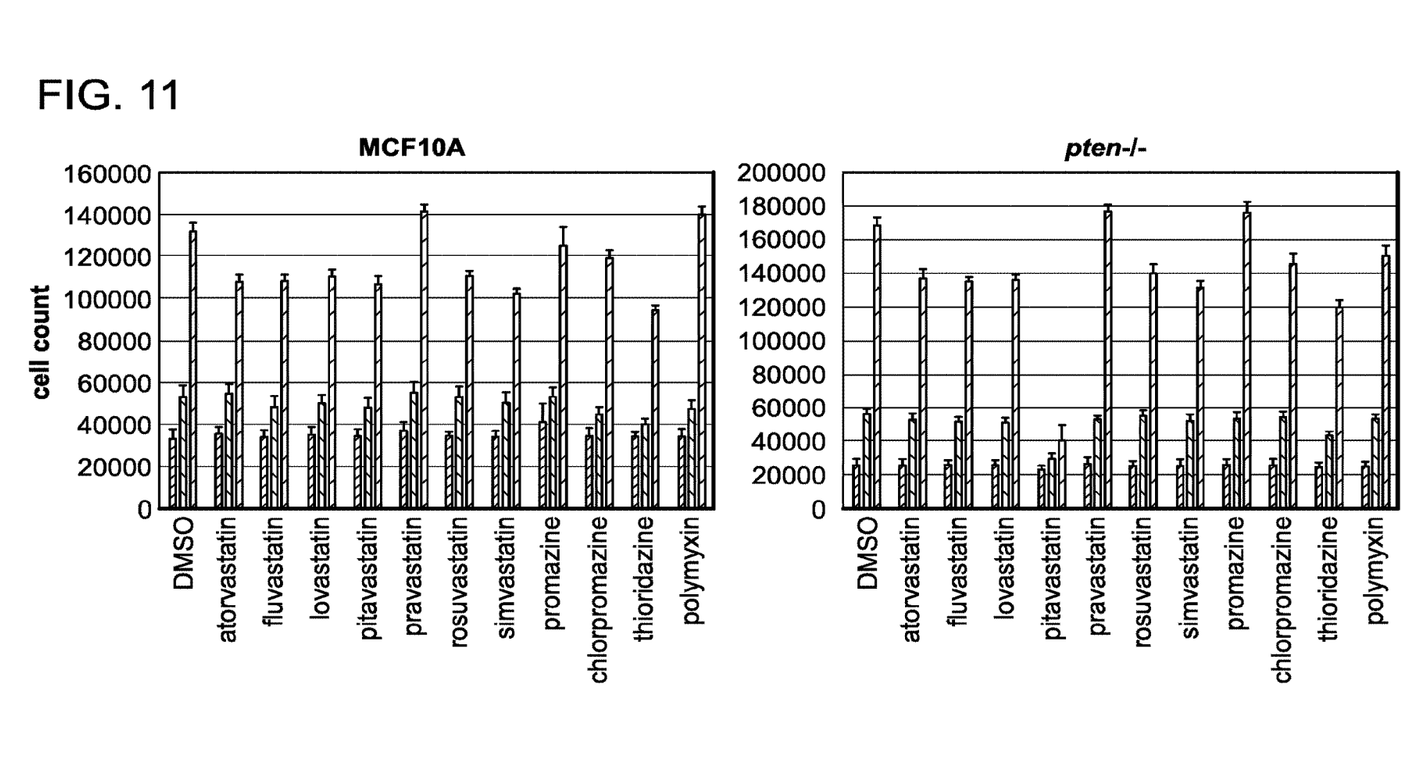
FIG. 11 are bar graphs showing that pitavastatin selectively inhibited the growth and survival of MCF-10A cells bearing a homozygous pten–/– deletion. Cells were treated with DMSO control or 5 µM drugs. Blue, orange, and yellow bars represent 20 hours, 44 hours, and 68 hours after drug treatment.

Example 6: Statins Induced Cell Death in Pre-Metastatic Cells and the Effects were Mediated Through the Geranylgeranyl Pathway To test whether the hits from the drug screen targeted human pre-metastatic cells, the growth of the human mammary epithelial cell lines MCF-10A, MCF-10A with homozygous pten deletion (pten−/−), or MCF10-A harboring oncogenic PIK3CA mutations under compound treatment were measured. At 5 μM, pitavastatin resulted in marked reduction in cell growth as well as extensive cell death in pten−/− as well as PIK3CA knock-in cells but not MCF-10A cells (FIG. 10 and FIG. 11, pten−/− shown as an example).

Figure 12A:
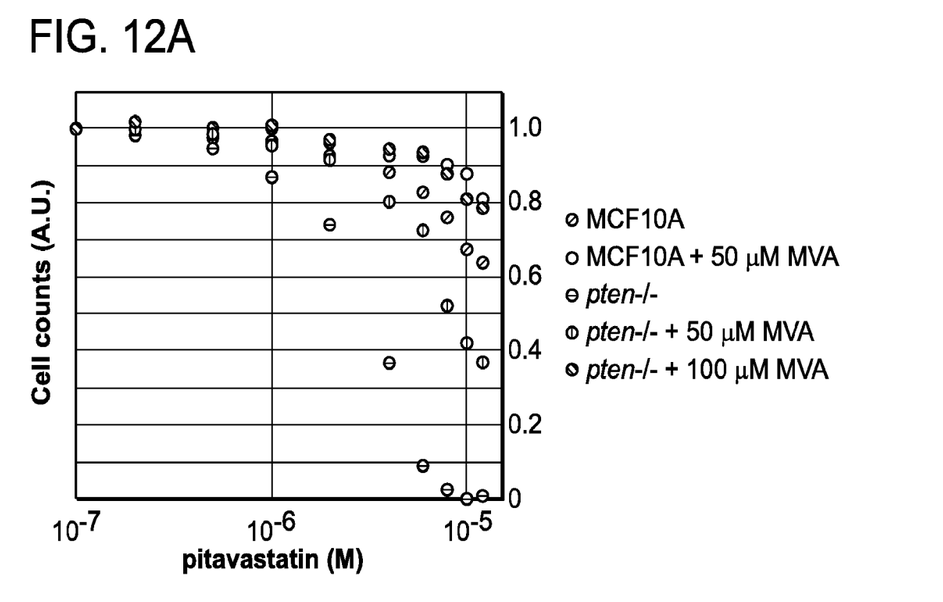
FIG. 12A and FIG. 12B are graphs showing that adding back mevalonic acid (MVA) and geranylgeranyl pyrophosphate (GGPP) blocked the toxic effects of pitavastatin on pten–/– cells. Cells were treated with increasing doses of pitavastatin in the presence or absence of MVA (FIG. 12A) and GGPP (FIG. 12B) at the indicated concentration.
Figure 12B:
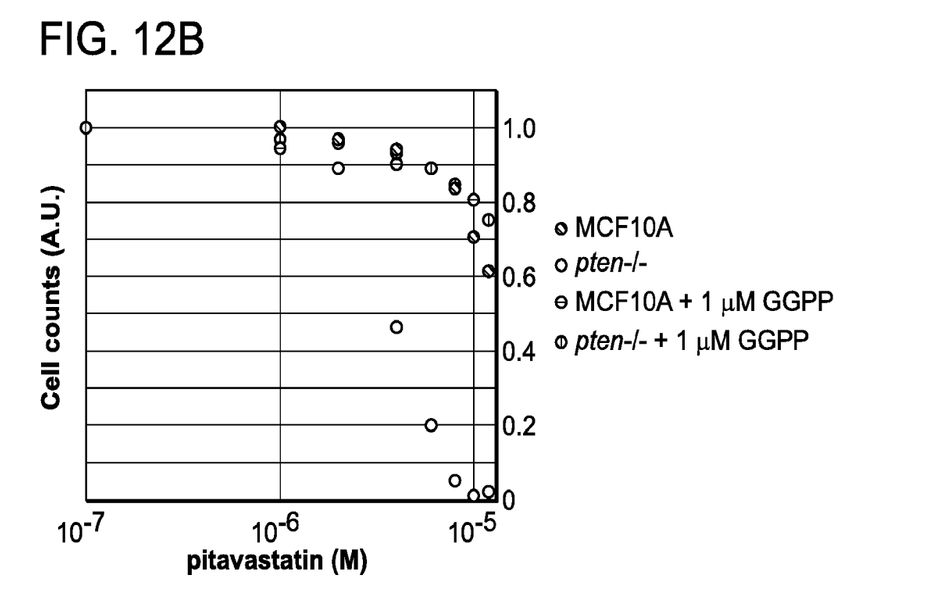

The use of statins is well established in the clinic to treat hypercholesterolemia by targeting HMG-CoA reductase that is responsible for cholesterol production. The mevalonate pathway is also the source of other biologically active metabolites such as farnesyl pyrophosphate (FPP) and geranylgeranyl pyrophosphate (GGPP), which are critical for posttranslational modifications of Ras and RhoA, respectively. To examine whether the cytotoxic effects of pitavastatin were due to decreased production of cholesterol or some other metabolites, add-back experiments were performed. Supplementation of either mevalonic acid (MVA), the enzymatic product of HMG-CoA reductase, or GGPP, but not cholesterol, completely blocked the effects of pitavastatin (FIG. 12). This observation revealed a distinct antitumorigenic mechanism of pitavastatin, which was segregated from its cholesterol lowering ability. It also indicated the use of statins as a therapeutic for tumor bearing mutations in PTEN or PI3K.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

We claim:

1. A method of killing a cell with an activated motility network comprising:
   stressing the cell or further activating or hyper-activating the cell's motility network,
   wherein an agent or stressor is administered to the cell thereby selectively killing the cell, wherein the cell bears a mutated oncogene or mutated tumor suppressor gene, wherein the mutated gene comprises Ras, PI3K, PTEN, or another defined mutation that activates a cell migration pathway, and the agent or stressor comprises an environmental perturbation.

2. The method of claim 1, wherein the environmental perturbation comprises a mechanical force, a temperature change, an electrical stimulus, a sound wave, osmotic shock, or other environmental change.

3. The method of claim 1, wherein the agent comprises a statin, a phenothiazine, an antibiotic, or an analgesic.

4. The method of claim 3, wherein the statin comprises pitavastatin, fluvastatin, atorvastatin, lovastatin, pravastatin, rosuvastatin, or simvastatin.

5. The method of claim 4, wherein the statin comprises pitavastatin.

6. The method of claim 3, wherein the phenothiazine comprises promazine HCl.

7. The method of claim 3, wherein the antibiotic comprises polymyxin B sulfate or chloroxine.

8. The method of claim 3, wherein the analgesic comprises phenazopyridine HCl.

9. The method of claim 1, wherein the agent is administered at concentration of 5 mg/kg- 25 mg/kg.

10. The method of claim 1, wherein the agent is administered orally, topically, or intravenously.

11. The method of claim 1, wherein the hyper-activation is sustained.

12. The method of claim 1, wherein the cell migration pathway comprises an oncogenic pathway or a tumor suppressor pathway.

13. The method of claim 12, wherein the tumor suppressor pathway comprises PTEN.

14. The method of claim 12, wherein the oncogenic pathway comprises Ras/TorC2, Rap or PI3K.

15. The method of claim 12, wherein the cell death by hyperactivation of a motility pathway is termed sparagmosis.

16. A method of killing a cell comprising:
administering to a cell an agent or stressor that selectively kills the cell, wherein the cell bears a mutated oncogene or mutated tumor suppressor gene, wherein the mutated gene comprises Ras, PI3K, PTEN, or another defined mutation that activates a cell migration pathway, and the agent or stressor comprises an environmental perturbation.

17. The method of claim 16, wherein the environmental perturbation comprises a mechanical force, a temperature change, an electrical stimulus, a sound wave, osmotic shock, or other environmental change.

18. The method of claim 16, wherein the agent comprises a statin, a phenothiazine, an antibiotic, or an analgesic.

19. The method of claim 16, wherein the agent is pitavastatin, fluvastatin, atorvastatin, lovastatin, pravastatin, rosuvastatin, or simvastatin.

20. A method of killing a cell, comprising:
treating the cell with an environmental perturbation that selectively kills the cell, wherein the cell bears a mutated oncogene or mutated tumor suppressor gene, wherein the mutated gene comprises Ras, PI3K, PTEN, or another defined mutation that activates a cell migration pathway.

21. The method of claim 20, wherein the environmental perturbation comprises a mechanical force, a temperature change, an electrical stimulus, a sound wave, osmotic shock, or other environmental change.

* * * * *